United States Patent [19]

Wheatley et al.

[11] Patent Number: 5,095,210

[45] Date of Patent: Mar. 10, 1992

[54] MULTILAYER FILM INDICATOR FOR DETERMINING THE INTEGRITY OR AUTHENTICITY OF AN ITEM AND PROCESS FOR USING SAME

[75] Inventors: John A. Wheatley; Walter J. Schrenk, both of Midland, Mich.

[73] Assignee: The Dow Chemical Company, Midland, Mich.

[21] Appl. No.: 506,036

[22] Filed: Apr. 6, 1990

[51] Int. Cl.⁵ .................. G01N 21/35; G06K 7/10
[52] U.S. Cl. ........................... 250/339; 250/341; 359/359; 356/71
[58] Field of Search ............. 356/71; 350/1.6; 250/339, 341

[56] References Cited

U.S. PATENT DOCUMENTS

| | | | |
|---|---|---|---|
| 3,858,977 | 1/1975 | Baird et al. | 356/71 |
| 4,094,947 | 6/1978 | Alfrey, Jr. et al. | 264/171 |
| 4,417,784 | 11/1983 | Knop et al. | 350/162.19 |
| 4,469,725 | 9/1984 | Fischer et al. | 428/13 |
| 4,489,318 | 12/1984 | Goldman | 356/71 |
| 4,516,679 | 5/1985 | Simpson et al. | 206/459 |
| 4,717,615 | 1/1988 | Reinhart | 428/161 |
| 4,721,217 | 1/1988 | Phillips et al. | 215/230 |
| 4,733,786 | 3/1988 | Emslander | 215/230 |
| 4,837,061 | 6/1989 | Smits et al. | 428/40 |
| 4,937,134 | 6/1990 | Schrenk et al. | 350/164 X |

OTHER PUBLICATIONS

Dobrowolski et al., "Research on Thin Film Anticounterfeiting Coatings at the National Research Council of Canada", Applied Optics, vol. 28, No. 14, 15, Jul. 1989, pp. 2702-2717.
Article "Multilayer Filters with Wide Transmittance Bands", vol. 53, No. 11, Jrnl of Optical Society of America, Nov. 1963.
Article "Reflectivity of Iridescent Coextruded Multilayered Plastic Films", vol. 13, No, 3, Polymer Engineering and Science, 1973.
Article, "Tamper Evident Packaging and Food", ASTM Standardization News, Mar. 1988.
Compilation, "Tamper Evident Packaging-A Literature Review", PIRA Information Services publication, pp. A85–88.

Primary Examiner—Vincent P. McGraw

[57] ABSTRACT

A multilayer film indicator, mechanism and process for using the indicator for determining the integrity, authenticity, or conformance of an item to an original state, involving the measurement and comparison of the condition of the indicator to an identifiable original quality of the indicator. The identifiable original quality of the indicator is produced by the optical interactions of layers of diverse thermoplastic materials within a laminate of the indicator and is not readily visible to the naked eye.

21 Claims, 1 Drawing Sheet

MULTILAYER FILM INDICATOR FOR DETERMINING THE INTEGRITY OR AUTHENTICITY OF AN ITEM AND PROCESS FOR USING SAME

BACKGROUND OF THE INVENTION

1. Field of the Invention

The present invention relates to indicators, and more particularly to indicators of the integrity or authenticity of an item or its conformance to an original state. In another aspect, the invention relates to a mechanism employing such indicators. In still another aspect, the invention relates to a process for determining the integrity or authenticity of an item or its conformance to an original state, involving the taking of measurements with respect to such an indicator.

2. Brief Description of the Prior Art

Previously known indicators of the integrity or authenticity of an item or its conformance to an original state have ranged from stamps and seals to watermarks, to holographic images or magnetic strips on credit cards, to shrink bands, membrane seals, metal breakaway caps, and blister packaging for food and drug items.

One difficulty with these former indicators is that one who would attempt to counterfeit, alter or tamper with items associated with these indicators is aware of the existence of an indicator, and of the success of the indicator in detecting such attempts as are described. This awareness of the existence and success of an indicator can lead to attempts to duplicate that indicator, some of these attempts perhaps being successful enough to evade immediate detection, and can make identification or capture of the individual counterfeiter or tamperer difficult.

For example, if a tamperer attempts to repair or hide the evidence of his tampering by reconstructing or duplicating a tamper evident, tamper resistant feature and is unsuccessful in doing so, the tamperer may not attempt to return the item to within the stream of commerce, so that the source and magnitude of a tampering problem is concealed from those persons who would be most affected by it and from those who could take corrective actions. In the meantime, the previously unsuccessful tamperer may find success with another item or product in perhaps another location.

With regard to the detection, monitoring and capture of persons engaged in espionage or counterfeiting in particular, the resources which may be available to such persons might be sufficient to reconstruct, duplicate or otherwise negate the presence of the aforementioned indicators. If these indicators are not readily perceived by the senses of sight and touch, for example, then these resources may not be brought to bear and the espionage or counterfeiting activities and persons responsible for those activities should be more easily detected, monitored and arrested.

It has been recognized that coextruded multilayer films having a mismatch in refractive indices between adjacent polymer layers can be made to selectively reflect near infrared, visible or ultraviolet wavelengths of light. It has also been suggested that when designing a film to reflect in the infrared, it may be possible to suppress higher order reflections which might enter into the visible range, see, e.g., "Reflectivity of Iridescent Coextruded Multilayer Plastic Films," Radford, Alfrey, Jr., and Schrenk, Polymer Engineering and Science, vol. 13, 3 (May 1973); U.S. Pat. No. 3,247,392 to Thelen; and "Multilayer Filters with Wide Transmittance Bands," Thelen, Journal of the Optical Society of America, vol. 53, 11 (1963). It has been further recognized that altering the overall thickness of such a multilayer film will alter the apparent color or selective reflectivity of such films, see U.S. Pat. No. 4,094,947 to Alfrey, Jr., et al.

The extension of these ideas to create a multilayer film indicator for indicating the integrity or authenticity of an item or its conformance to an original state has not been suggested where the indicator includes a laminate having closely adjacent layers of two or more diverse thermoplastic materials of differing refractive indices associated with the item and having an identifiable original quality arising from the optical interactions of these layers of diverse materials. More specifically, such a multilayer film indicator has not been suggested which in an initial condition is substantially colorless but which has an identifiable original reflectance spectrum, and which produces and retains evidence of strain of a selected extent and greater which is not visible to the naked eye of an observer.

In view of the shortcomings of the prior art, both with specific regard to the previously known tamper evident, tamper resistant packaging materials and generally to indicators of the integrity or authenticity of an item or its conformance to an original state generally, it can be seen that there is a compelling need for such an indicator and for such a packaging material that do not alert one who would tamper with or counterfeit an item of the indicator's existence either before, during or after the tampering has taken place, that provides a safe and reliable means for detecting attempts at tampering or counterfeits, and that, moreover, is relatively inexpensive while being difficult to defeat, duplicate or replace.

SUMMARY OF THE INVENTION

The present invention fulfills these needs and overcomes the shortcomings of the prior art by providing a multilayer film indicator for indicating the integrity or authenticity of an item or its conformance to an original state, including a laminate associated with the item as by affixation thereto or embossing thereon, by attachment to a container associated with the item or to a companion article, or by attachment to a label associated with the item, for example. The laminate comprises closely adjacent layers of two or more diverse thermoplastic materials of different refractive indices, and is possessed of an identifiable original quality arising from the optical interactions of these layers. One such identifiable original quality would be an identifiable original reflectance spectrum.

It should be noted that the "diverse thermoplastic materials" need not differ in any respect except in terms of refractive index. Thus, while adjacent layers of materials may be chemically diverse, if such materials are of the same refractive index then for purposes of the present invention they are not "diverse". Similarly, adjacent layers may be virtually identical in every other respect save for refractive index, yet they are to be considered "diverse" for purposes of this disclosure.

The present invention also provides a process for determining the integrity or authenticity of an item or its conformance to an original state, which comprises the steps of associating a multilayer film indicator of the present invention with the item, measuring an identifiable original quality such as a reflectance spectrum of the multilayer film indicator, measuring the laminate a second time to obtain a second measurement of the laminate with respect to the original quality, and comparing the original and the second measurements to ascertain the presence or absence of the identifiable original quality in a way which would confirm the integrity or authenticity of an item or its conformance to an original state. The process is useful where a delivery of the item and associated indicator to the custody of another is to occur, or when the item remains at the disposition of a single party who may wish to periodically monitor the item in question to ensure its continued integrity.

In another aspect, our invention relates generally to a mechanism for determining the integrity or authenticity of an item or its conformance to an original state, wherein an indicator of the present invention includes a laminate of diverse thermoplastic materials having an identifiable original quality which is not readily visible to the naked eye and acts in cooperative combination with means for comparing the condition of the laminate with the original quality. This means for comparing the condition of the laminate with the original quality can include a written description or illustration of the original quality and can also include equipment for measuring the laminate and thereby ascertaining its condition, preparatory to making a comparison with the original quality as previously known to the person making the comparison or as communicated to that person by the above-mentioned written description or by some other means.

DETAILED DESCRIPTION OF THE PREFERRED EMBODIMENT

For multilayer films having a period of P layers, it has been previously determined that the primary reflectance of normally incident light occurs at a wavelength $\lambda_0$, wherein $$\lambda_0 = 2 \sum_{i=1}^{P} (n_i d_i),$$

and $(n_i d_i)$ represents the optical thickness of a given layer, or the product of a refractive index and physical thickness associated with that layer.

Higher orders of reflectance occur at wavelengths determined by the equation $$\lambda_M = \frac{(\lambda_0)}{M},$$

where M is the order of reflectance. For example, if the primary reflectance $\lambda_0$ is at 1400 nanometers, then subsequent orders of reflectance will occur at 700 nanometers (second order), 467 nanometers (third order), 350 nanometers (fourth order), and so on.

The inventors of the present invention have applied these concepts in relation to a particular embodiment of the present invention, and have discovered that a multilayer film indicator could be constructed for indicating the integrity or authenticity of an item or its conformance to an original state, which includes a laminate of closely adjacent layers of two or more diverse thermoplastic materials of differing refractive indices associated with the item and having an identifiable original quality arising from the optical interactions of these layers, such as an identifiable original reflectance spectrum. Preferably, these interactive layers should be of a substantially continuous nature, and should be "closely adjacent" at least in the sense of presenting an area of overlap to incident light.

In a more particular application, the inventors have discovered that such a multilayer film indicator could be constructed which in an initial condition is substantially colorless, but which when strained to a selected extent will produce and retain evidence of such strain which is not readily visible to the naked eye of an observer.

Figure 1:
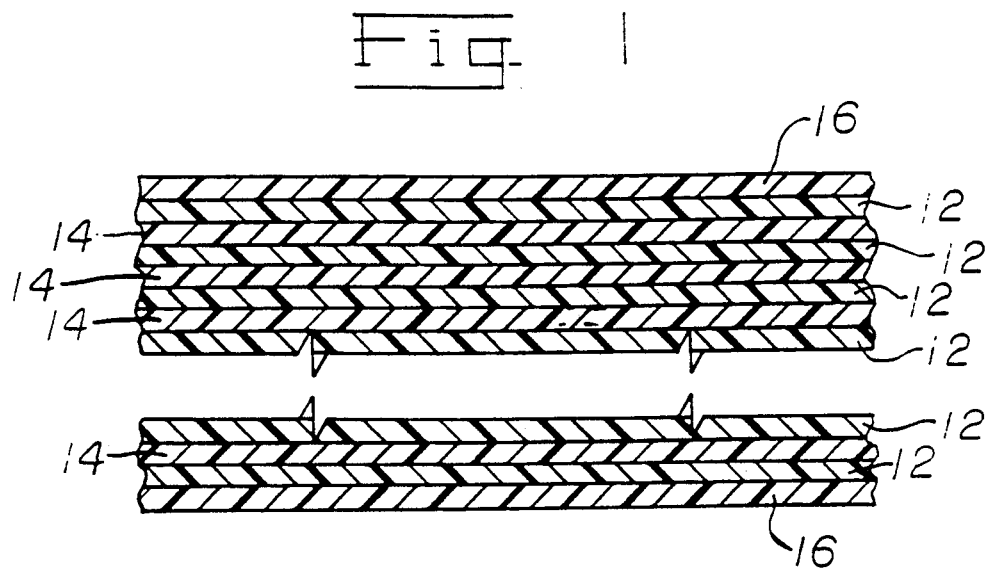
FIG. 1 is a cross-sectional view of a preferred embodiment of the multilayer film indicator of the present invention.

Referring now to the drawings, and more particularly to FIG. 1, a preferred multilayer film indicator 10 of the present invention is illustrated. The indicator 10 shown in FIG. 1 includes layers 12 and 14 of two diverse thermoplastic materials A and B in an ABAB-type layer order, wherein the layers 12 correspond to layers of a material A, and the layers 14 to an optically diverse material, B.

The indicator 10 of FIG. 1 also includes outer skin layers 16 which in the preferred embodiments are primarily included and are sufficiently thick to prevent excessive breakup of the thin layers 12 and 14 of A and B in processing and making the indicator 10 by the preferred multilayer coextrusion processes, there being generally in the indicators of the present invention preferably at least about fifty substantially continuous layers of the various diverse materials comprising the laminate. The preferred multilayer coextrusion processes are taught, for example, in commonly assigned U.S. Pat. Nos. 3,565,985 and 3,773,882, the disclosures of which are hereby incorporated herein by reference.

The outer skin layers 16 may be present also for structural properties if desired. An example of an application where the skin layers 16 would fulfill a structural purpose might be where the laminate of closely adjacent layers 12 and 14 is incorporated into the wall of a plastic or plastic-encased article otherwise comprised at least in part of the skin layers 16.

To insure that the films of the present invention do not duplicate some of the shortcomings of the prior art, namely the visible nature of the indicator either before, during or after an attempt to tamper with the item associated with the indicator, the films of the present invention are preferably designed such that in an initial condition, the primary reflectance $\lambda_0$ of the film shown in FIG. 1, for example, is in the infrared range or more preferably in the ultraviolet range of the visible light spectrum. It would also be possible to have the indicators reflect color as long as the presence of color does not of itself signal to a tamperer/counterfeiter that an indicator of attempts at tampering or counterfeiting is present. It is expected that usually the indicators will be colorless, however, and should be applied to a surface without conspicuously altering the appearance of the surface and drawing attention to its presence, as for example by presenting a glossy finish where the remainder of the article has a matte finish.

Accordingly, the optical thicknesses of the layers of A and B are such that within a period AB of the two component films of the present invention, $\lambda_0 = 2(n_A d_A + n_B d_B)$ is less than about 0.4 micrometers or greater than about 0.7 micrometers. Further, where the indicators are expected to undergo some degree of strain, the indicators of the present invention should preferably be designed so that in an initial condition they are substantially colorless, and when strained to a selected extent will produce and retain evidence of such strain without that evidence being readily visible to the naked eye of an observer.

Thus, where the indicators have been constructed so that the primary reflectance $\lambda_0$ is greater than about 0.7 micrometers (i.e., they are essentially infrared-reflecting), the indicators will have been designed so that a degree of strain involved in an attempt at tampering or the like will not cause strong higher orders of reflectance to fall into the visible range.

Figure 2:
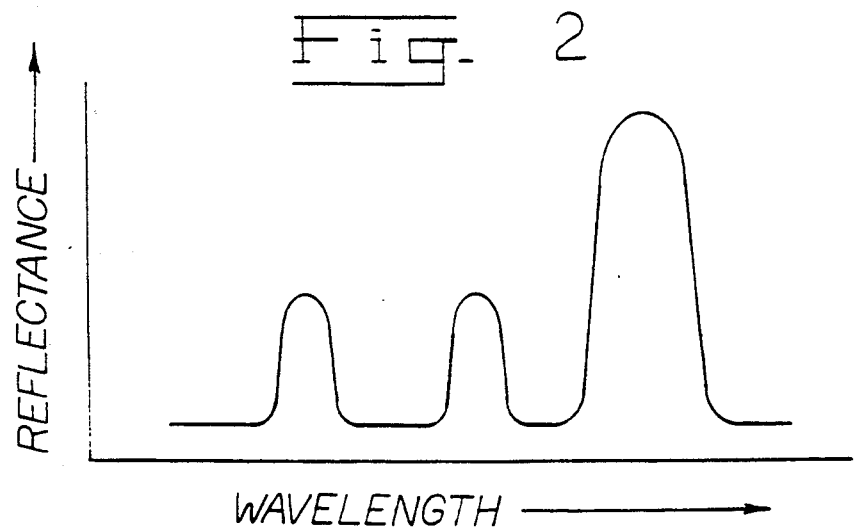
FIG. 2 is a representation of a reflectance spectrum of an indicator of the present invention in an initial condition.
Figure 3:
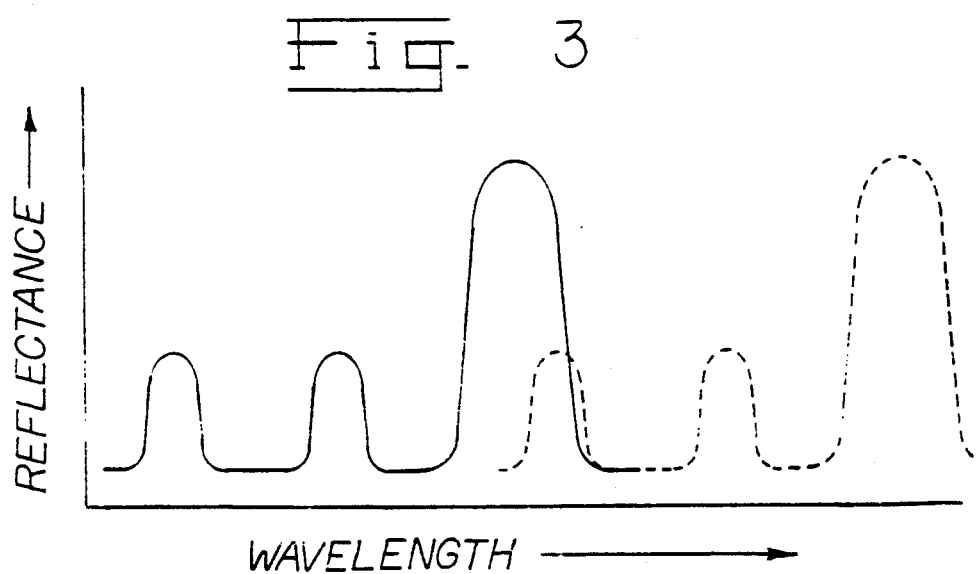
FIG. 3 is a representation of the reflectance spectrum of FIG. 2 after the corresponding indicator of FIG. 2 has been strained beyond a selected extent.

It will be appreciated in this respect that straining the indicators of the present invention will cause the layer thicknesses $d_A$ and $d_B$ to decrease at least locally, so that the primary reflectance at the area of straining of the indicator will occur at a lower wavelength. In turn, the higher orders of reflectance will also be shifted downward in the spectrum, as shown in FIGS. 2 and 3. The designer of the indicators of the present invention will preferably take into account this anticipated shift in the reflectance spectrum and the comparative strengths of the higher orders of reflectance, and either design the indicators for a degree of strain sufficiently in excess of that which could be reasonably anticipated to thus provide a safety factor, or design the indicators so that higher orders of reflectance do not occur strongly or are suppressed. These skills are well within the capabilities of the person of ordinary skill in the art.

The relative absence of color thus sought, both in an initial state and upon the application of a degree of strain, is thought to be principally the means by which the indicator's existence and effectiveness will be disguised or hidden from the person or party attempting to tamper with or counterfeit the item with which the indicator is associated. Where the application of the indicator involves a particularly sensitive area, as in matters relating to the detection of espionage and the like, an extra margin of safety consistent with the above description of the design of such indicators may be desirable in terms of the design of the infrared-reflecting film indicators.

As noted previously, the indicators of the present invention which are expected to undergo strain should when strained to a selected extent produce and retain evidence of such strain which is not readily visible to the naked eye of an observer. The evidence of strain is preferably preserved in the indicator by the yield point of at least one of the diverse thermoplastic materials being at least equaled when the shift in the reflectance spectrum associated with the straining and tampering of an indicator, as opposed to the shift associated with accidental handling strains and the like, is produced.

In this manner, the attempt at tampering or counterfeiting is memorialized in the indicator, without the indicator having alerted the person or parties attempting to tamper with or counterfeit an item associated with the indicator of the indicator's existence.

The skin layers 16, which are provided again primarily to protect the thin film layers 12 and 14 from excessive layer breakup in processing and manufacturing, should not themselves make the indicators of the present invention visible to a person or party attempting to tamper with an item either before, during or after the attempted tampering. Accordingly, the skin layers 16 are generally sufficiently thick so as not to optically interact with the remainder of the layers, and are preferably transparent to visible light.

The skin layers 16 may conceivably be omitted altogether. Because of the very small physical thicknesses of the hundreds of layers which have thus far been used to develop the indicators, however, it has been thought necessary to employ skin layers 16 in actual practice which comprise from about 5 to about 10 percent by volume of the indicators at least, and as noted earlier it may be desirable to have skin layers of this thickness or greater for structural purposes.

Indicators which have such a large number of thin layers will, it is believed, be virtually impossible for a tamperer or counterfeiter to reproduce without detailed knowledge of its manufacture which presumably will not be available to him, even where the existence of such an indicator is ultimately discovered. For this reason, the multilayer coextrusion processes of the type mentioned above are considered particularly adapted to the practice of the present invention.

The two component embodiment which has thus far been primarily described is generally considered satisfactory for purposes of the present invention, but embodiments having additional components and layers of diverse materials could be used generally to provide a more distinctive original quality by which the laminate of the indicator may be identified, and/or to provide a greater complexity to the indicator's construction and thus a greater barrier to its effective replacement and counterfeiting. The same design considerations as detailed above with respect to an infrared-reflecting two-component indicator will apply with equal force to these infrared-reflecting multiple component indicators.

Of course, if the multilayer film indicators are designed to have optical thicknesses providing a primary reflectance peak in the ultraviolet range, the degree of strain which is expected is basically immaterial in terms of producing a shift into the visible range, and is material only to the preservation of evidence of such strain in at least equaling the yield point of one of the two or more diverse materials comprising the indicator.

Because one need not worry about higher order reflections for films initially reflecting in the ultraviolet, such films are generally presently preferred over those initially reflecting in the infrared. These ultraviolet-reflecting films are also considered somewhat simpler to make, in that such films may be made by merely drawing down conventional thicker films to the point where all color disappears from these films, without worrying about whether enough "room" has been left for a certain degree of strain without a display of some color in the film, how much strain should be anticipated and so forth.

Oriented films which undergo the application of heat and which experience an associated relieving of stress and increase in film thickness may provide an exception, however, in that the primary reflectance of these films will occur at higher rather than lower wavelengths after an attempt at tampering. Provided measures are also undertaken with respect to these films that would prevent them from reflecting visible light, such films can thus be used as indicators of an attempt at tampering involving the application of heat or more generally as indicators of the thermal history of an article.

Aside from considerations of their visual appearance, the indicators of the present invention should not be so physically thick that in use they might be readily detected by the sense of touch, as might occur in some uses where an indicator is designed to initially reflect high in the infrared region. Where the indicator in question is isolated and attached to something, the indicator should preferably not be detectable as a "bump" on that something. Where underlying a coating or skin layer which is transparent to visible light, the indicator should preferably also not be detectable as a "bump", and the coating or skin layer should preferably flow over and around the indicator so as to make the indicator of a comparable thickness with respect to its immediate surroundings.

It may be in some cases that the degree of strain which is to be encountered may not be known. In this case, an alternative approach for the infrared reflecting films would select the materials such that the film would rupture before a degree of strain would occur such as would create a shift sufficient to produce readily noticeable color in the indicator. This might also eliminate any concerns about the indicator being so thick as to be readily sensed by touch, since no real safety factor would theoretically be required in the form of a very large gap between the primary reflectance peak of the indicator and the upper end of the visible range. This would not be a satisfactory approach, however, with the present invention where the rupture of the film itself could be detected, assuming this would not be acceptable. One can imagine instances where the detection of the rupture of the indicator would not be of particular concern.

For example, consider the use of an indicator of the present invention as a transparent, colorless, heat shrinkable tamper evident, tamper resistant packaging material wrapped around the screw cap and neck of an aspirin bottle, or more generally as joined to two portions of an item which are movable with respect to one another. The tamperer of such an item could assume, once the colorless band is broken, that the band may be relatively easily duplicated with any other colorless wrap without leaving evidence of tampering. In this instance it is of no concern that the rupture of the indicator is detected since the rupture itself would not give rise to a suspicion on the part of the tamperer of the true nature of the packaging material. Thus the tamperer would presumably not abandon his attempt, and the indicator is telling evidence of such an attempt merely by its absence.

The selection of one of these approaches to designing the multilayer film indicators of the present invention will vary from use to use and is considered significantly dependent on the sophistication of the tamperer or counterfeiter of a given item, so that it is impossible to set a hard and fast rule for all such uses. It is believed, however, that the preceding discussion will enable this choice to be rationally and reasonably made.

With respect to achieving and preserving evidence of strain produced within certain of the multilayer film indicators of the present invention, there are several possible constructions which would be suitable. One possible configuration would place at least one material whose yield point is exceeded when the evidence is produced within the core layers of a multilayer film indicator having optically inactive skin layers.

Another configuration would encapsulate core layers comprised of elastomeric materials within skin layers whose yield point would be at least equaled when the shift in reflectance spectra or other evidentiary event occurs, thus preventing the elastomeric inner or core layers from returning to an unstretched or unstrained condition. As noted earlier, the film indicators of the present invention may not employ skin layers at all.

However constructed, the multilayer film indicators of the present invention are well adapted for a number of uses, and are particularly well suited for use as a tamper evident, tamper resistant packaging material, as for example in the form of a shrink band joined to two portions of an item which are movable with respect to one another such as the neck and screw cap of a prescription bottle, or as a membrane seal across an opening in a container. Or, the films may be used to overwrap an item entirely. It may also be desirable to employ the films of the present invention in two or all three of these capacities.

The mechanism provided for performing the process of the present invention utilizes a multilayer indicator as described above with an identifiable original quality which is not readily visible to the naked eye, in cooperative combination with means for comparing the condition at a given point in time of the laminate of the indicator with the original quality produced by the laminate.

This means for comparing the condition of the laminate and thus of the indicator with the original quality to detect any departure from that original quality can include a written description or illustration of the original quality, as for example a printed copy of an original reflectance spectrum. The means can also include equipment for measuring the laminate with respect to the original quality, so that for the reflectance spectrum just mentioned the means would further comprise a spectrophotometer.

The manner of use of the indicators and mechanism of the present invention is simple and straightforward. Where the step of associating an indicator with an item is performed by a single person with the intent of periodically monitoring the indicator, that person would take an initial measurement with some sort of equipment for accomplishing this task, take a subsequent measurement, and compare the two measurements.

For uses such as in authenticating a document or other written communication where the person who is initially in custody of the item and indicator differs from the person who will receive the item under circumstances warranting a determination of the integrity or authenticity of the item, the "fingerprint" of the indicator will generally have been communicated in writing to the recipient of the item either previously or contemporaneously and separately from the delivery of the item itself. It is also considered that an oral communication of the essential identifiable quality, as in the communication of the major peaks and magnitudes of reflectance, might suffice so long as the information transmitted is sufficiently specific so that any attempts at replicating the indicator which could fairly be expected given the level of sophistication of the supposed counterfeiter could be detected.

The present invention has been primarily directed to providing and retaining reliable evidence from the optical interactions of the film layers in a multilayer laminate comprised of two or more diverse thermoplastic materials, which evidence would indicate something of the integrity, authenticity or conformity of an item associated with the laminate to an original state, and which evidence would not be readily apparent to a person or party attempting to tamper with or counterfeit the item. One measure of evidence which has been suggested is the monitoring of an identifiable reflectance spectrum of the laminate, although any measurable effect relating to the optical interactions of layers within the laminate which would change with an attempt at tampering or counterfeiting should suffice. Finally, it can be seen that the multilayer film indicators of the present invention are adapted for use with a variety of items and may be associated with these items in any number of ways, and further that adequate indicators are capable of being easily and inexpensively manufactured by conventional techniques and conventional equipment.

The indicators and process for using the same which are provided are thus well adapted to achieve the objects of the present invention, to overcome the shortcomings of the prior art, and to realize advantages with respect to the prior art. While preferred embodiments of the present invention have been described, it is apparent that a number of changes may be made to the indicators and process of the present invention without departing in scope therefrom. These changes are to be considered encompassed within the scope of the present invention, as defined by the claims which follow.

What is claimed is:

1. A process for determining the integrity or authenticity of an item or its conformance to an original state, including the steps of:
    associating a multilayer film indicator with said item, wherein the multilayer film indicator comprises a laminate of closely adjacent layers of two or more diverse thermoplastic materials of differing refractive indices which has an identifiable original quality arising from the optical interactions of the layers, such quality not being readily visible to the naked eye;
    measuring the original quality;
    measuring the laminate a second time; and
    comparing the original and the second measurements to ascertain the presence or absence of the identifiable original quality.

2. A process as defined in claim 1, wherein the identifiable original quality is an identifiable original reflectance spectrum.

3. A process as defined in claim 1, wherein the second measurement follows a delivery of the item to the custody of another.

4. A multilayer film indicator associated with an item for indicating the integrity or authenticity of the item or its conformance to an original state, which in an initial condition is substantially colorless, and which when strained to a selected extent will produce and retain evidence of such strain which is not readily visible to the naked eye of an observer, including a laminate of closely adjacent layers of two or more diverse thermoplastic materials of differing refractive indices having an identifiable reflectance spectrum.

5. An indicator as defined in claim 4, wherein the evidence includes a shift in the identifiable reflectance spectrum of said indicator.

6. An indicator as defined in claim 5, wherein the yield point of at least one of the diverse thermoplastic materials has been at least equaled when the shift is produced.

7. An indicator as defined in claim 4, wherein the film indicator will rupture with a degree of additional strain while the evidence is still not readily visible to the naked eye of an observer.

8. A tamper evident, tamper resistant packaging material which includes an indicator as defined in claim 4.

9. An item which has been at least partially packaged within an indicator as defined in claim 4, such that the indicator has been joined to two portions of the item which are movable with respect to one another.

10. An item which has been embossed with an indicator as defined in claim 4.

11. A mechanism for determining the integrity or authenticity of an item or its conformance to an original state, including in cooperative combination:
    a multilayer film indicator associated with the item and which includes a laminate of closely adjacent layers of two or more diverse thermoplastic materials of differing refractive indices having an identifiable original quality arising from the optical interactions of said layers which is not readily visible to the naked eye; and
    means for comparing the condition of said laminate with the original quality.

12. A mechanism as defined in claim 11, wherein the identifiable original quality of the laminate of the multilayer film indicator is an identifiable original reflectance spectrum.

13. A mechanism as defined in claim 12, wherein said laminate consists essentially of at least one period of layers of a first thermoplastic material A having a refractive index $n_A$ and an average layer thickness $d_A$ and of a second thermoplastic material B having a refractive index $n_B$ and an average layer thickness $d_B$ in an ABAB-type layer order.

14. A mechanism as defined in claim 13, wherein $\lambda_0 = 2(n_A d_A + n_B d_B)$ is less than about 0.4 micrometers or greater than about 0.7 micrometers.

15. A mechanism as defined in claim 14, wherein the laminate further includes outer skin layers which are transparent to visible light.

16. A mechanism as defined in claim 11, wherein:
    the layers of the two or more diverse thermoplastic materials in the laminate of the indicator are arranged in one or more periods of P layers; and $$\lambda_0 = 2 \sum_{i=1}^{P} (n_i d_i)$$

is less than about 0.4 micrometers.

17. A mechanism as defined in claim 11, wherein the means for comparing the condition of the laminate with the original reflectance spectrum includes a printed copy of the reflectance spectrum.

18. A mechanism as defined in claim 17, wherein the means for comparing the condition of the laminate with the original reflectance spectrum further includes a spectrophotometer.

19. A mechanism as defined in claim 11, wherein the means for comparing the condition of the laminate with the original quality includes a written description or illustration of the original quality.

20. A mechanism as defined in claim 19, wherein said written description or illustration is intended to be previously or contemporaneously but separately communicated to one who is to employ the means for comparing the condition of the laminate with the original quality.

21. A mechanism as defined in claim 11, wherein the means for comparing the condition of the laminate with the original quality includes equipment for measuring the laminate with respect to the original quality.

* * * * *